US006844321B2

(12) United States Patent
Arentsen

(10) Patent No.: US 6,844,321 B2
(45) Date of Patent: Jan. 18, 2005

(54) CRYSTALLIZATION OF A GLP-1 ANALOGUE

(75) Inventor: Anne Charlotte Arentsen, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 425 days.

(21) Appl. No.: 09/769,692

(22) Filed: Jan. 25, 2001

(65) Prior Publication Data

US 2003/0186858 A1 Oct. 2, 2003

Related U.S. Application Data

(60) Provisional application No. 60/183,300, filed on Feb. 17, 2000.

(30) Foreign Application Priority Data

Jan. 31, 2000 (DK) ........................................ 2000 00156

(51) Int. Cl.[7] ........................ A61K 38/00; A61K 38/26; C07K 16/00
(52) U.S. Cl. ........................... 514/12; 514/54; 530/308; 530/324; 530/422; 530/427
(58) Field of Search ..................... 514/12, 54; 530/308, 530/324, 422, 427

(56) References Cited

U.S. PATENT DOCUMENTS 4,683,202 A 7/1987 Mullis .................... 435/91

FOREIGN PATENT DOCUMENTS

| EP | 0 619 322 | * | 10/1994 |
| EP | 0 619 322 A2 | | 10/1994 |
| EP | 0699686 | | 3/1996 |
| WO | WO 87/06941 | | 11/1987 |
| WO | WO 90/11296 | | 10/1990 |
| WO | WO 97/46584 | | 12/1997 |
| WO | WO 98/08871 | * | 3/1998 |
| WO | WO 99/30731 | * | 6/1999 |
| WO | WO 99/43708 | | 9/1999 |

OTHER PUBLICATIONS

Pridal et al., International Journal of Pharmaceutics, vol. 136, pp. 53–59, 1996.*

Beaucage and Caruthers, Deoxynucleoside Phosphoramidites–A New Class of Key Intermediates For Deoxypolynucleotide Synthesis vol. 22, No. 20, pp 1859–1862, (1981).

Matthes et al., Simultaneous Rapid Chemical Synthesis Of Over One Hundred Oligonucleotides On A Microscale, EMBO Journal vol. 3 No. 4 Pp. 801–805., (1984).

Saiki et al., "Primer–Directed Enzymatic Amplification Of DNA With A Thermostable DNA Polymerase", Science 239 pp. 487–491 (1988).

Lone Pridal et al: "Absorption of glucagons–like peptide–1 can be protracted by zinc or protamine"—International Journal of Pharmaceutics vol. 136, pp. 53–59 (1996).

* cited by examiner

*Primary Examiner*—Jon Weber
*Assistant Examiner*—Abdel A. Mohamed
(74) *Attorney, Agent, or Firm*—Richard W. Book, Esq.; Reza Green, Esq.; Marc A. Began, Esq.

(57) ABSTRACT

Crystals of glucagon-like peptide-1 (GLP-1) and GLP-1 analogues, and processes for preparation of crystals of GLP-1 and GLP-1 analogues.

37 Claims, No Drawings

SEQUENCE LISTING

```
<160> NUMBER OF SEQ ID NOS: 1
<210> SEQ ID NO 1
<211> LENGTH: 39
<212> TYPE: PRT
<213> ORGANISM: Homo Sapien
<220> FEATURE:
<221> NAME/KEY: VARIANT
<222> LOCATION: (1)...(39)
<223> OTHER INFORMATION: Xaa = any amino acid

<400> SEQUENCE: 1

His Xaa Xaa Gly Xaa Phe Thr Xaa Asp Xaa Xaa Xaa Xaa Xaa Xaa
 1               5                  10                  15

Xaa Xaa Xaa Xaa Xaa Phe Ile Xaa Xaa Xaa Xaa Xaa Xaa Xaa Xaa
                20                  25                  30

Xaa Xaa Xaa Xaa Xaa Xaa Xaa
                35
```

CRYSTALLIZATION OF A GLP-1 ANALOGUE

CROSS-REFERENCE TO RELATED APPLICATIONS

This application claims priority under 35 U.S.C. 119 of United States provisional application No. 60/183,300 filed on Feb. 17, 2000 and Danish application no PA 2000 00156 filed on Jan. 31, 2000, the contents of which are fully incorporated herein by reference.

The present invention relates to novel crystals of GLP-1 and analogues thereof, such as needle shaped crystals, and processes for the preparation of crystals of GLP-1 and analogues thereof.

BACKGROUND

The hormones regulating insulin secretion belong to the so-called enteroinsular axis, designating a group of hormones, released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1). Because of its insulinotropic effect, GIP, isolated in 1973 (1) immediately attracted considerable interest among diabetologists. However, numerous investigations carried out during the following years clearly indicated that a defective secretion of GIP was not involved in the pathogenesis of insulin-dependent diabetes mellitus (IDDM) or non-insulin-dependent diabetes mellitus (NIDDM) (2). Furthermore, as an insulinotropic hormone, GIP was found to be almost ineffective in NIDDM (2). The other incretin hormone, GLP-1 is the most potent insulinotropic substance known (3). Unlike GIP, it is surprisingly effective in stimulating insulin secretion in NIDDM patients. In addition, and in contrast to the other insulinotropic hormones (perhaps with the exception of secretin) it also potently inhibits glucagon secretion. Because of these actions it has pronounced blood glucose lowering effects particularly in patients with NIDDM.

DESCRIPTION OF THE INVENTION

Human GLP-1 is a 37 amino acid residue peptide originating from preproglucagon which is synthesised i.a. in the L-cells in the distal ileum, in the pancreas and in the brain. Processing of preproglucagon to give GLP-1(7–36)amide, GLP-1(7–37) and GLP-2 occurs mainly in the L-cells. A simple system is used to describe fragments and analogues of this peptide. Thus, for example, $Gly^8$-GLP-1(7–37) designates a fragment of GLP-1 formally derived from GLP-1 by deleting the amino acid residues Nos. 1 to 6 and substituting the naturally occurring amino acid residue in position 8 (Ala) by Gly. Similarly, $Lys^{34}(N^\epsilon$-tetradecanoyl)-GLP-1 (7–37) designates GLP-1(7–37) wherein the $\epsilon$-amino group of the Lys residue in position 34 has been tetradecanoylated.

GLP-1 and analogues thereof can be produced by a method which comprises culturing or fermenting a host cell containing a DNA sequence encoding the GLP-1 analogue and capable of expressing said analogue in a suitable nutrient medium under conditions permitting the expression of the peptide, after which the resulting GLP-1 analogue is recovered from the culture or fermentation broth.

The implementation of a crystallisation step in the manufacturing process for the preparation of a GLP-1 analogue resulted in removal of coloured compounds (coloured impurities) from the fermentation broth, reduction of yeast host cell proteins, such as *Saccharomyces cerevisiae* proteins (SCP) as well as removal of water, and low loss of the GLP-1 analog from the mother liquor.

The GLP-1 analog was then re-dissolved and further purified by conventional High Performance Cation Exchange Chromatography (HP-CIEC) and Reverse Phase High Performance Liquid Chromatography (RP-HPLC) followed by a second crystallisation step at the pI of the GLP-1 analogue. Hereafter, the analogue was acylated, e.g. as disclosed in WO 98/08871, and the resulting solution containing mono-acylated GLP-1 analogue was further purified by conventional RP-HPLC and finally precipitated at pI of the mono-acylated GLP-1 analogue.

Thus, the resulting crystals are an important and useful intermediate product in the manufacturing process for preparing a GLP-1 analogue and for preparing a mono-acylated GLP-1 analogue. The resulting crystals of the GLP-1 analogue are also useful in the preparation of a pharmaceutical composition, such as an injectable drug, comprising the crystals and a pharmaceutically acceptable carrier.

Accordingly, the present invention relates to a process for producing crystals of a GLP-1 analogue comprising:

a) preparing an aqueous solution comprising a GLP-1 analogue, a salt, and an organic solvent, and b) isolating the crystals after formation.

The GLP-1 analogue to be crystallized in step a) is either substantially pure or is impure. The purity can be measured by analytical HPLC and/or capillary electrophoresis.

In step a) a buffer may optionally be added to said solution. Usually it is most convenient to add a buffer to the solution, such as any buffer including but not limited to: citrate buffers, phosphate buffers, tris buffers, bis-Tris buffer, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof. The concentration of buffer added is easily decided by the skilled practitioner using his common general knowledge, but will usually be in the range from 0 mM to 100 mM, such as 0.5 mM to 50 mM, e.g. 5–10 mM.

Further in step a) pH of the solution may be adjusted by means of an acid or base to keep it constant or it may vary, provided that pI of the GLP-1 analogue is not reached. Usually it is most convenient to adjust pH with an acid, e.g. HCl, if pH of the aqueous solution is above the isoelectric point (hereinafter pI) of the GLP-1 analogue, or with a base, e.g. NaOH, if pH of the aqueous solution is below the pI of the GLP-1 analogue. The pH of the solution is easily decided by the skilled practitioner using his common general knowledge, but will usually be within a certain range from the pI of the GLP-1 analogue, such as between about pI–4 (id est, pI minus 4) and pI or between about pI and pI+4 (id est pI plus 4), depending on whether the aqueous solution of the GLP-1 analogue is below the pI or above the pI. The pH of the aqueous solution may be adjusted relatively far from the pI of the GLP-1 analogue, such as at about pI–4 or pI+4 and then, optionally, by step or linear gradient, be driven towards the pI until formation of crystals occur, in particular needle shaped crystals. In case of the GLP-1 analogue being Arg$^{34}$GLP-1(7–37), having a pI of about 5.4, it is preferred to prepare an aqueous solution of Arg$^{34}$GLP-1(7–37) above pI, preferably at about pH 8.5–9.5, and then adjust the pH to about pH 6–7 with an acid, e.g. HCl. In one embodiment of the invention the pH is adjusted so that pI-4<pH<pI, preferably pI-2<pH<pI. In another embodiment of the invention the pH is adjusted so that pI<pH<pI+4, preferably pI<pH<pI+2.

Further in step a) an excipient may optionally be added that influence the stability or solubility of the GLP-1 analogue.

In one embodiment of the invention the crystals are needle shaped crystals of a GLP-1 analogue having a length of at least 0.5 µm. In another embodiment of the invention the crystals are needle shaped crystals of a GLP-1 analogue having a length of at least 2 µm. In a further embodiment of the invention the crystals are needle shaped crystals of a GLP-1 analogue having a length of at least 8 µm. In a further embodiment of the invention the crystals are needle shaped crystals of a GLP-1 analogue having a length of 0.5 µm to 50 µm, such as 2 µm to 50 µm, e.g. 2 µm to 30 µm. In a further embodiment of the invention the crystals are needle shaped crystals of a GLP-1 analogue having a length of 8 µm to 50 µm.

In another embodiment of the invention the GLP-1 analogue to be crystallized has a purity of less than 98%, as measured by HPLC. In a further embodiment of the invention the GLP-1 analogue to be crystallized has a purity of less than 95%, such as less than 90%, as measured by HPLC.

In another embodiment of the invention the GLP-1 analogue to be crystallized has a purity of more than 20%, such as more than 30%, as measured by HPLC. In a further embodiment of the invention the GLP-1 analogue to be crystallized has a purity between 20% and 90%, such as a purity between 20% and 50%, as measured by HPLC.

In a further embodiment of the invention the GLP-1 analogue in the aqueous solution is present in a concentration of at least 0.5 mg/ml.

In a further embodiment of the invention the GLP-1 analogue in the aqueous solution is present in a concentration of from 0.5 mg/ml to 20 mg/ml, such as 2–10 mg/ml.

In a further embodiment of the invention the GLP-1 analogue is selected from non-synthetic GLP-1 analogues.

In a further embodiment of the invention the GLP-1 analogue is selected from the Thr$^8$, Met$^8$, Gly$^8$ and Val$^8$ analogues of GLP-1(7–37) and GLP-1(7–36) amide, more preferred the Gly$^8$ and Val$^8$ analogues of GLP-1(7–37) and GLP-1(7–36) amide, most preferred the Val$^8$ analogues of GLP-1(7–37) and GLP-1(7–36) amide.

In a further embodiment of the invention the GLP-1 analogue has the formula II:

```
                                              (SEQ ID: NO 1)
    7   8   9  10  11  12  13  14  15  16  17
  His-Xaa-Xaa-Gly-Xaa-Phe-Thr-Xaa-Asp-Xaa-Xaa- 18  19  20  21  22  23  24  25  26  27  28
  Xaa-Xaa-Xaa-Xaa-Xaa-Xaa-Xaa-Xaa-Xaa-Xaa-Phe- 29  30  31  32  33  34  35  36  37  38
  Ile-Xaa-Xaa-Xaa-Xaa-Xaa-Xaa-Xaa-Xaa-Xaa 39  40  41  42  43  44  45
  Xaa-Xaa-Xaa-Xaa-Xaa-Xaa-Xaa (II)
``` wherein

Xaa at position 8 is Ala, Gly, Ser, Thr, Leu, Ile, Val, Glu, Asp, Met, or Lys,

Xaa at position 9 is Glu, Asp, or Lys,

Xaa at position 11 is Thr, Ala, Gly, Ser, Leu, Ile, Val, Glu, Asp, or Lys,

Xaa at position 14 is Ser, Ala, Gly, Thr, Leu, Ile, Val, Glu, Asp, or Lys,

Xaa at position 16 is Val, Ala, Gly, Ser, Thr, Leu, Ile, Tyr, Glu, Asp, or Lys,

Xaa at position 17 is Ser, Ala, Gly, Thr, Leu, Ile, Val, Glu, Asp, or Lys,

Xaa at position 18 is Ser, Ala, Gly, Thr, Leu, Ile, Val, Glu, Asp, or Lys,

Xaa at position 19 is Tyr, Phe, Trp, Glu, Asp, or Lys,

Xaa at position 20 is Leu, Ala, Gly, Ser, Thr, Leu, Ile, Val, Glu, Asp, or Lys,

Xaa at position 21 is Glu, Asp, or Lys,

Xaa at position 22 is Gly, Ala, Ser, Thr, Leu, Ile, Val, Glu, Asp, or Lys,

Xaa at position 23 is Gln, Asn, Arg, Glu, Asp, or Lys,

Xaa at position 24 is Ala, Gly, Ser, Thr, Leu, Ile, Val, Arg, Glu, Asp, or Lys,

Xaa at position 25 is Ala, Gly, Ser, Thr, Leu, Ile, Val, Glu, Asp, or Lys,

Xaa at position 26 is Lys, Arg, Gln, Glu, Asp, or His,

Xaa at position 27 is Glu, Asp, or Lys,

Xaa at position 30 is Ala, Gly, Ser, Thr, Leu, Ile, Val, Glu, Asp, or Lys,

Xaa at position 31 is Trp, Phe, Tyr, Glu, Asp, or Lys,

Xaa at position 32 is Leu, Gly, Ala, Ser, Thr, Ile, Val, Glu, Asp, or Lys,

Xaa at position 33 is Val, Gly, Ala, Ser, Thr, Leu, Ie, Glu, Asp, or Lys,

Xaa at position 34 is Lys, Arg, Glu, Asp, or His,

Xaa at position 35 is Gly, Ala, Ser, Thr, Leu, Ile, Val, Glu, Asp, or Lys,

Xaa at position 36 is Arg, Lys, Glu, Asp, or His,

Xaa at position 37 is Gly, Ala, Ser, Thr, Leu, Ile, Val, Glu, Asp, or Lys, or is deleted, Xaa at position 38 is Arg, Lys, Glu, Asp, or His, or is deleted, Xaa at position 39 is Arg, Lys, Glu, Asp, or His, or is deleted, Xaa at position 40 is Asp, Glu, or Lys, or is deleted, Xaa at position 41 is Phe, Trp, Tyr, Glu, Asp, or Lys, or is deleted, Xaa at position 42 is Pro, Lys, Glu, or Asp, or is deleted, Xaa at position 43 is Glu, Asp, Lys, or is deleted, Xaa at position 44 is Glu, Asp, or Lys, or is deleted, and Xaa at position 45 is Val, Glu, Asp, or Lys, or is deleted, or (a) a C-1-6-ester thereof, (b) amide, C-1-6-alkylamide, or C-1-6-dialkylamide thereof and/or (c) a pharmaceutically acceptable salt thereof, provided that (i) when the amino acid at position 37, 38, 39, 40, 41, 42, 43 or 44 is deleted, then each amino acid downstream of the amino acid is also deleted.

In a further embodiment of the GLP-1 analogue of formula II, the amino acids at positions 37–45 are absent.

In another embodiment of the GLP-1 analogue of formula II, the amino acids at positions 38–45 are absent.

In another embodiment of the GLP-1 analogue of formula II, the amino acids at positions 39–45 are absent.

In another embodiment of the GLP-1 analogue of formula II, Xaa at position 8 is Ala, Gly, Ser, Thr, Met, or Val.

In another embodiment of the GLP-1 analogue of formula II, Xaa at position 8 is Gly, Thr, Met, or Val.

In another embodiment of the GLP-1 analogue of formula II, Xaa at position 8 is Val.

In another embodiment of the GLP-1 analogue of formula II, Xaa at position 9 is Glu.

In another embodiment of the GLP-1 analogue of formula II, Xaa at position 11 is Thr.

In another embodiment of the GLP-1 analogue of formula II, Xaa at position 14 is Ser.

In another embodiment of the GLP-1 analogue of formula II, Xaa at position 16 is Val.

In another embodiment of the GLP-1 analogue of formula II, Xaa at position 17 is Ser.

In another embodiment of the GLP-1 analogue of formula II, Xaa at position 18 is Ser, Lys, Glu, or Asp.

In another embodiment of the GLP-1 analogue of formula II, Xaa at position 19 is Tyr, Lys, Glu, or Asp.

In another embodiment of the GLP-1 analogue of formula II, Xaa at position 20 is Leu, Lys, Glu, or Asp.

In another embodiment of the GLP-1 analogue of formula II, Xaa at position 21 is Glu, Lys, or Asp.

In another embodiment of the GLP-1 analogue of formula II, Xaa at position 22 is Gly, Glu, Asp, or Lys.

In another embodiment of the GLP-1 analogue of formula II, Xaa at position 23 is Gln, Glu, Asp, or Lys.

In another embodiment of the GLP-1 analogue of formula II, Xaa at position 24 is Ala, Glu, Asp, or Lys.

In another embodiment of the GLP-1 analogue of formula II, Xaa at position 25 is Ala, Glu, Asp, or Lys.

In another embodiment of the GLP-1 analogue of formula II, Xaa at position 26 is Lys, Glu, Asp, or Arg.

In another embodiment of the GLP-1 analogue of formula II, Xaa at position 27 is Glu, Asp, or Lys.

In another embodiment of the GLP-1 analogue of formula II, Xaa at position 30 is Ala, Glu, Asp, or Lys.

In another embodiment of the GLP-1 analogue of formula II, Xaa at position 31 is Trp, Glu, Asp, or Lys.

In another embodiment of the GLP-1 analogue of formula II, Xaa at position 32 is Leu, Glu, Asp, or Lys.

In another embodiment of the GLP-1 analogue of formula II, Xaa at position 33 is Val, Glu, Asp, or Lys.

In another embodiment of the GLP-1 analogue of formula II, Xaa at position 34 is Lys, Arg, Glu, or Asp.

In another embodiment of the GLP-1 analogue of formula II, Xaa at position 35 is Gly, Glu, Asp, or Lys.

In another embodiment of the GLP-1 analogue of formula II, Xaa at position 36 is Arg, Lys, Glu, or Asp.

In another embodiment of the GLP-1 analogue of formula II, Xaa at position 37 is Gly, Glu, Asp, or Lys.

In another embodiment of the GLP-1 analogue of formula II, Xaa at position 38 is Arg, or Lys, or is deleted.

In another embodiment of the GLP-1 analogue of formula II, Xaa at position 39 is deleted.

In another embodiment of the GLP-1 analogue of formula II, Xaa at position 40 is deleted.

In another embodiment of the GLP-1 analogue of formula II, Xaa at position 41 is deleted.

In another embodiment of the GLP-1 analogue of formula II, Xaa at position 42 is deleted.

In another embodiment of the GLP-1 analogue of formula II, Xaa at position 43 is deleted.

In another embodiment of the GLP-1 analogue of formula II, Xaa at position 44 is deleted.

In another embodiment of the GLP-1 analogue of formula II, Xaa at position 45 is deleted.

In another embodiment of the GLP-1 analogue of formula II, Xaa at position 26 is Arg, each of Xaa at positions 37–45 is deleted, and each of the other Xaa is the amino acid in native GLP-1(7–36).

In another embodiment of the GLP-1 analogue of formula II, Xaa at position 26 is Arg, each of Xaa at positions 38–45 is deleted, and each of the other Xaa is the amino acid in native GLP-1(7–37).

In another embodiment of the GLP-1 analogue of formula II, Xaa at position 26 is Arg, each of Xaa at positions 39–45 is deleted, and each of the other Xaa is the amino acid in native GLP-1(7–38).

In another embodiment of the GLP-1 analogue of formula II, Xaa at position 34 is Arg, each of Xaa at positions 37–45 is deleted, and each of the other Xaa is the amino acid in native GLP-1(7–36).

In another embodiment of the GLP-1 analogue of formula II, Xaa at position 34 is Arg, each of Xaa at positions 38–45 is deleted, and each of the other Xaa is the amino acid in native GLP-1(7–37).

In another embodiment of the GLP-1 analogue of formula II, Xaa at position 34 is Arg, each of Xaa at positions 39–45 is deleted, and each of the other Xaa is the amino acid in native GLP-1(7–38).

In another embodiment of the GLP-1 analogue of formula II, Xaa at positions 26 and 34 is Arg, Xaa at position 36 is Lys, each of Xaa at positions 37–45 is deleted, and each of the other Xaa is the amino acid in native GLP-1(7–36).

In another embodiment of the GLP-1 analogue of formula II, Xaa at positions 26 and 34 is Arg, Xaa at position 36 is Lys, each of Xaa at positions 38–45 is deleted, and each of the other Xaa is the amino acid in native GLP-1(7–37).

In another embodiment of the GLP-1 analogue of formula II, Xaa at positions 26 and 34 is Arg, Xaa at position 36 is Lys, each of Xaa at positions 39–45 is deleted, and each of the other Xaa is the amino acid in native GLP-1(7–38).

In another embodiment of the GLP-1 analogue of formula II, Xaa at positions 26 and 34 is Arg, Xaa at position 38 is Lys, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly, or Val, Xaa at position 37 is Glu, Xaa at position 36 is Lys, each of Xaa at positions 38–45 is deleted, and each of the other Xaa is the amino acid in native GLP-1(7–37).

In another embodiment of the GLP-1 analogue of formula II, Xaa at position 8 is Thr, Ser, Gly, or Val, Xaa at position 37 is Glu, Xaa at position 36 is Lys, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly or Val, Xaa at position 37 is Glu, Xaa at position 38 is Lys, each of Xaa at positions 39–45 is deleted, and each of the other Xaa is the amino acid in native GLP-1(7–38).

In another embodiment of the GLP-1 analogue of formula II, Xaa at position 18, 23 or 27 is Lys, and Xaa at positions 26 and 34 is Arg, each of Xaa at positions 37–45 is deleted, and each of the other Xaa is the amino acid in native GLP-1(7–36).

In another embodiment of the GLP-1 analogue of formula II, Xaa at position 18, 23 or 27 is Lys, and Xaa at positions 26 and 34 is Arg, each of Xaa at positions 38–45 is deleted, and each of the other Xaa is the amino acid in native GLP-1(7–37).

In another embodiment of the GLP-1 analogue of formula II, Xaa at position 18, 23 or 27 is Lys, and Xaa at positions 26 and 34 is Arg, each of Xaa at positions 39–45 is deleted, and each of the other Xaa is the amino acid in native GLP-1(7–38).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 37–45 is deleted, and each of the other Xaa is the amino acid in native GLP-1(7–36).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 38–45 is deleted, and each of the other Xaa is the amino acid in native GLP-1(7–37).

In another embodiment of the GLP-1 analogue of formula II, Xaa at position 8 is Thr, Ser, Gly, or Val, Xaa at position 18, 23 or 27 is Lys, and Xaa at position 26 and 34 is Arg, each of Xaa at positions 39–45 is deleted, and each of the other Xaa is the amino acid in native GLP-1(7–38).

Such GLP-1 analogues of formula II includes, but is not limited to, $Arg^{26}$-GLP-1(7–37);

$Arg^{34}$-GLP-1(7–37); $Lys^{36}$-GLP-1(7–37); $Arg^{26,34}Lys^{36}$-GLP-1(7–37); $Arg^{26,34}Lys^{38}$-GLP-1(7–38);

$Arg^{26,34}Lys^{39}$-GLP-1(7–39); $Arg^{26,34}Lys^{40}$-GLP-1(7–40); $Arg^{26}Lys^{36}$-GLP-1(7–37); $Arg^{34}Lys^{36}$-GLP-1(7–37); $Arg^{26}Lys^{39}$-GLP-1(7–39); $Arg^{34}Lys^{40}$-GLP-1(7–40); $Arg^{26,34}Lys^{36,39}$-GLP-1(7–39);

$Arg^{26,34}Lys^{36,40}$-GLP-1(7–40); $Gly^8Arg^{26}$-GLP-1(7–37); $Gly^8Arg^{34}$-GLP-1(7–37); $Val^8$-GLP-1(7–37);

$Thr^8$-GLP-1(7–37); $Gly^8$-GLP-1(7–37); $Met^8$-GLP-1(7–37); $Gly^8Lys^{36}$-GLP-1(7–37);

$Gly^8Arg^{26,34}Lys^{36}$-GLP-1(7–37); $Gly^8Arg^{26,34}Lys^{39}$-GLP-1(7–39); $Gly^8Arg^{26,34}Lys^{40}$-GLP-1(7–40);

$Gly^8Arg^{26}Lys^{36}$-GLP-1(7–37); $Gly^8Arg^{34}Lys^{36}$-GLP-1(7–37); $Gly^8Arg^{26}Lys^{39}$-GLP-1(7–39);

$Gly^8Arg^{34}Lys^{40}$-GLP-1(7–40); $Gly^8Arg^{26,34}Lys^{36,39}$-GLP-1(7–39); $Gly^8Arg^{26,34}Lys^{36,40}$-GLP-1(7–40);

$Arg^{26,34}Lys^{38}$GLP-1(7–38); $Arg^{26,34}Lys^{39}$GLP-1(7–39); $Arg^{26,34}Lys^{40}$-GLP-1(7–40);

$Arg^{26,34}Lys^{41}$GLP-1(7–41); $Arg^{26,34}Lys^{42}$GLP-1(7–42); $Arg^{26,34}Lys^{43}$GLP-1(7–43); $Arg^{26,34}Lys^{44}$GLP-1(7–44); $Arg^{26,34}Lys^{45}$GLP-1(7–45); $Arg^{26,34}Lys^{38}$GLP-1(1–38); $Arg^{26,34}Lys^{39}$GLP-1(1–39);

$Arg^{26,34}Lys^{40}$GLP-1(1–40); $Arg^{26,34}Lys^{41}$GLP-1(1–41); $Arg^{26,34}Lys^{42}$GLP-1(1–42); $Arg^{26,34}Lys^{43}$GLP-1(1–43); $Arg^{26,34}Lys^{44}$GLP-1(1–44); $Arg^{26,34}Lys^{45}$GLP-1(1–45); $Arg^{26,34}Lys^{38}$GLP-1(2–38);

$Arg^{26,34}Lys^{39}$GLP-1(2–39); $Arg^{26,34}Lys^{40}$GLP-1(2–40); $Arg^{26,34}Lys^{41}$GLP-1(2–41); $Arg^{26,34}Lys^{42}$GLP-1(2–42); $Arg^{26,34}Lys^{43}$GLP-1(2–43); $Arg^{26,34}Lys^{44}$GLP-1(2–44); $Arg^{26,34}Lys^{45}$GLP-1(2–45);

$Arg^{26,34}Lys^{38}$GLP-1(3–38); $Arg^{26,34}Lys^{39}$GLP-1(3–39); $Arg^{26,34}Lys^{40}$GLP-1(3–40); $Arg^{26,34}Lys^{41}$GLP-1(3–41); $Arg^{26,34}Lys^{42}$GLP-1(3–42); $Arg^{26,34}Lys^{43}$GLP-1(3–43); $Arg^{26,34}Lys^{44}$GLP-1(3–44);

$Arg^{26,34}Lys^{45}$GLP-1(3–45); $Arg^{26,34}Lys^{38}$GLP-1(4–38); $Arg^{26,34}Lys^{39}$GLP-1(4–39); $Arg^{26,34}Lys^{40}$GLP-1(4–40); $Arg^{26,34}Lys^{41}$GLP-1(4–41); $Arg^{26,34}Lys^{42}$GLP-1(4–42); $Arg^{26,34}Lys^{43}$GLP-1(4–43);

$Arg^{26,34}Lys^{44}$GLP-1(4–44); $Arg^{26,34}Lys^{45}$GLP-1(4–45); $Arg^{26,34}Lys^{38}$GLP-1(5–38); $Arg^{26,34}Lys^{39}$GLP-1(5–39); $Arg^{26,34}Lys^{40}$GLP-1(5–40); $Arg^{26,34}Lys^{41}$GLP-1(5–41); $Arg^{26,34}Lys^{42}$GLP-1(5–42);

$Arg^{26,34}Lys^{43}$GLP-1(5–43); $Arg^{26,34}Lys^{44}$GLP-1(5–44); $Arg^{26,34}Lys^{45}$GLP-1(5–45); $Arg^{26,34}Lys^{38}$GLP-1(6–38); $Arg^{26,34}Lys^{39}$GLP-1(6–39); $Arg^{26}34Lys^{40}$GLP-1(6–40); $Arg^{26,34}Lys^{41}$GLP-1(6–41);

$Arg^{26,34}Lys^{42}$ GLP-1(6–42); $Arg^{26,34}Lys^{43}$GLP-1(6–43); $Arg^{26,34}Lys^{44}$GLP-1(6–44); $Arg^{26,34}Lys^{45}$GLP-1(6–45); $Arg^{26}Lys^{38}$GLP-1(1–38); $Arg^{34}Lys^{38}$GLP-1(1–38); $Arg^{26,34}Lys^{36,38}$GLP-1(1–38);

$Arg^{26}Lys^{38}$GLP-1(7–38); $Arg^{34}Lys^{39}$GLP-1(7–38); $Arg^{26,34}Lys^{36,38}$GLP-1(7–38); $Arg^{26,34}Lys^{38}$GLP-1(7–38); $Arg^{26}Lys^{39}$GLP-1(1–39); $Arg^{34}Lys^{39}$GLP-1(1–39); $Arg^{26,34}Lys^{36,39}$GLP-1(1–39);

$Arg^{26}Lys^{39}$GLP-1(7–39); $Arg^{34}Lys^{39}$GLP-1(7–39) and $Arg^{26,34}Lys^{36,39}$GLP-1(7–39); Each one of these specific GLP-1 analogues constitutes an alternative embodiment of the invention.

In a further embodiment of the invention the GLP-1 analogue has the formula III

A-HN-GLP-1(8-B)-X (III)

wherein

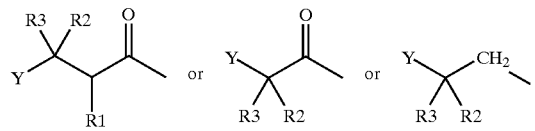

wherein $R^1$, $R^2$ and $R^3$ are independently H, lower alkyl having 1 to 6 carbon atoms, optionally substituted phenyl, $NH_2$, NH—CO-(lower alkyl), —OH, lower alkoxy having 1 to 6 carbon atoms, halogen, $SO_2$-(lower alkyl) or $CF_3$, said phenyl is optionally substituted with at least one group selected from $NH_2$, —OH, lower alkyl or lower alkoxy having 1–6 carbon atoms, halogen, $SO_2$-(lower alkyl), NH—CO-(lower alkyl) or $CF_3$, or $R^1$ and $R^2$ may together form a bond; Y is a five or six membered ring system selected from the group consisting of:

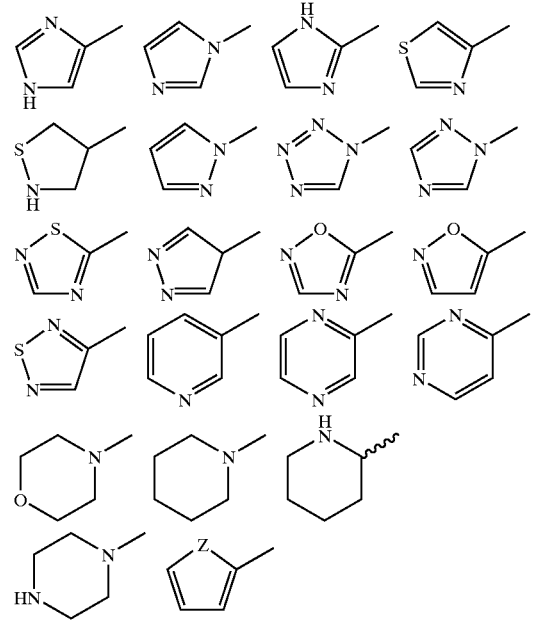

wherein Z is N, O or S, said ring system is optionally substituted with one or more functional groups selected from the group consisting of $NH_2$, $NO_2$, OH, $C_{1-6}$ alkyl, $C_{1-6}$ alkoxy, halogen (Cl, Br, F, I), $CF_3$ and aryl;

B is an integer in the range of 35–45; and

X is —OH, —NH$_2$, or a C$_{1-6}$ alkyl amide or C$_{1-6}$ dialkyl amide group; or an analogue thereof.

Such GLP-1 analogues of formula III includes, but is not limited to

Arg$^{26}$-GLP-1(7–37); Arg$^{34}$-GLP-1(7–37); Lys$^{36}$-GLP-1(7–37);

Arg$^{26,34}$Lys$^{36}$-GLP-1(7–37); Arg$^{26,34}$Lys$^{38}$GLP-1(7–38);

Arg$^{26,34}$Lys$^{39}$-GLP-1(7–39); Arg$^{26,34}$Lys$^{40}$-GLP-1(7–40);

Arg$^{26}$Lys$^{36}$-GLP-1(7–37); Arg$^{34}$Lys$^{36}$-GLP-1(7–37);

Arg$^{26}$Lys$^{39}$-GLP-1(7–39); Arg$^{34}$Lys$^{40}$-GLP-1(7–40);

Arg$^{26,34}$Lys$^{36,39}$-GLP-1(7–39); Arg$^{26,34}$Lys$^{36,40}$-GLP-1(7–40);

Gly$^8$Arg$^{26}$-GLP-1(7–37); Gly$^8$Arg$^{34}$-GLP-1(7–37);

Gly$^8$Lys$^{36}$-GLP-1(7–37); Gly$^8$Arg$^{26,34}$Lys$^{36}$-GLP-1(7–37);

Gly$^8$Arg$^{26,34}$Lys$^{39}$-GLP-1(7–39); Gly$^8$Arg$^{26,34}$Lys$^{40}$-GLP-1(7–40);

Gly$^8$Arg$^{26}$Lys$^{36}$-GLP-1(7–37); Gly$^8$Arg$^{34}$Lys$^{36}$-GLP-1(7–37);

Gly$^8$Arg$^{26}$Lys$^{39}$-G LP-1(7–39); Gly$^8$Arg$^{34}$Lys$^{40}$-GLP-1(7–40);

Gly$^8$Arg$^{26,34}$Lys$^{36,39}$-GLP-1(7–39); or

Gly$^8$Arg$^{26,34}$Lys$^{36,40}$-GLP-1(7–40). Each one of these specific GLP-1 analogues constitutes an alternative embodiment of the invention.

In a further embodiment of the invention the GLP-1 analogue has the formula IV

A-GLP-1(19-B)-X            (IV)

wherein

A is a peptide comprising the amino acid residues of GLP-1(8–18) or a fragment thereof;

B is an integer in the range of 35–45; and

X is —OH, —NH$_2$, or a C$_{1-6}$ alkyl amide or C$_{1-6}$ dialkyl amide group; or an analogue thereof.

In an embodiment of the GLP-1 analogue of formula IV, A is a peptide selected from the group consisting of GLP-1(8–18), GLP-1(9–18), GLP-1(10–18), GLP-1(11–18), GLP-1(12–18), GLP-1(13–18), GLP-1(14–18), GLP-1(15–18), GLP-1(16–18), GLP-1(17–18) and GLP-1(18). Preferably, A is GLP-1(8–18), GLP-1(9–18), GLP-1(10–18), GLP-1(11–18) or GLP-1(12–18), and B is 36, 37 or 38. Most preferably, A is GLP-1(8–18).

In a further embodiment of the GLP-1 analogue of formula IV, B is 35, 36, 37, 38, 39, 40, 41, 42, 43 or 44. In a more preferred embodiment, B is 36. In another more preferred embodiment. B is 37. In another more preferred embodiment, B is 38.

Such GLP-1 analogues of formula IV includes, but is not limited to

Arg$^{26}$-GLP-1(8–37); Arg$^{34}$-GLP-1(8–37); Lys$^{36}$-GLP-1(8–37);

Arg$^{26,34}$Lys$^{36}$-GLP-1(8–37); Arg$^{26,34}$Lys$^{38}$GLP (8–38);

Arg$^{26,34}$Lys$^{39}$-GLP-1(8–39); Arg$^{26,34}$Lys$^{40}$-GLP-1(8–40);

Arg$^{26}$Lys$^{36}$-GLP-1(8–37); Arg$^{34}$Lys$^{36}$-GLP-1(8–37);

Arg$^{26}$Lys$^{39}$-GLP-1(8–39); Arg$^{34}$Lys$^{40}$-GLP-1(8–40);

Arg$^{26,34}$Lys$^{36,39}$-GLP-1(8–39); Arg$^{26,34}$Lys$^{36,40}$-GLP-1(8–40);

Gly$^8$Arg$^{26}$-GLP-1(8–37); Gly$^8$Arg$^{34}$-GLP-1(8–37);

Gly$^8$Lys$^{36}$-GLP-1(8–37); Gly$^6$Arg$^{26,34}$Lys$^{36}$-GLP-1(8–37);

Gly$^8$Arg$^{26,34}$Lys$^{39}$-GLP-1(8–39); Gly$^8$Arg$^{26,34}$Lys$^{40}$-GLP-1(8–40);

Gly$^8$Arg$^{26}$Lys$^{36}$-GLP-1(8–37); Gly$^8$Arg$^{34}$Lys$^3$-GLP-1(8–37);

Gly$^8$Arg$^{26}$Lys$^{39}$-GLP-1(8–39); Gly$^8$Arg$^3$Lys$^{40}$-GLP-1(8–40);

Gly$^8$Arg$^{26,34}$Lys$^{36,39}$-GLP-1(8–39); or

Gly$^8$Arg$^{26,34}$Lys$^{36,40}$-GLP-1(8–40). Each one of these specific GLP-1 analogues constitutes an alternative embodiment of the invention.

In a further embodiment of the invention the GLP-1 analogue is Arg$^{26}$GLP-1(7–37).

In a further embodiment of the invention the GLP-1 analogue is Arg$^{34}$GLP-1(7–37).

In a further embodiment of the invention the salt is present in a concentration of at least 25 mM. In a further embodiment of the invention the salt is present in a concentration of from 25 mM to 800 mM, such as 100 to 200 mM. The salt may be added to the aqueous solution comprising the GLP-1 analogue all at once or as a step or linear gradient.

In a further embodiment of the invention the salt is selected from inorganic salts. Such inorganic salts, includes but is not limited to chlorides, bromides, fluorides, iodides, sulphates or nitrates with ammonium, alkaline metals or earth alkaline metals, or mixtures thereof, e.g. NaCl, KCl, NH$_4$Cl, CaCl$_2$, sodium sulphate, ammonium nitrate, potassium sulphate, ammonium sulphate, or mixtures thereof.

In a further embodiment of the invention the salt is selected from organic salts. Such organic salts, includes but is not limited to acetates, citrates or tartrates with ammonium, alkaline metals or earth alkaline metals, or mixtures thereof, e.g. sodium acetate, potassium acetate, ammonium acetate, sodium citrate, potassium citrate, potassium tartrate, ammonium citrate, calcium acetate or mixtures thereof.

In a further embodiment of the invention the organic solvent is present in a concentration of at least 0.5% (vol/vol). In a further embodiment of the invention the organic solvent is present in a concentration of from 0.5 to 50% (vol/vol), such as 1 to 15% (vol/vol). The organic solvent may be added to the aqueous solution comprising the GLP-1 analogue all at once or as a step or linear gradient.

In a further embodiment of the invention the organic solvent is selected from C$_{1-6}$-alkanol, C$_{1-6}$-alkenol, C$_{1-6}$-alkynol, urea, guanidine, C$_{1-6}$-alkanoic acid, ketone, DMSO, C$_{2-6}$-glycol, C$_{3-7}$-polyalcohol including sugars, or mixtures thereof. Each of these solvents constitutes an individual embodiment of the invention.

In a further embodiment of the invention the organic solvent is selected from C$_{1-6}$-alkanol, ketone or C$_{3-7}$-polyalcohol including sugars.

In a further embodiment of the invention the organic solvent is selected from methanol, ethanol, n-propanol, allyl alcohol, n-butanol, n-pentanol, n-hexanol, 2-propanol, tert-butyl alcohol, 1,2-ethanediol, 1,2-propanediol, 2-methyl-2,4-pentanediol, glycerol, methylethyl ketone or acetone. Each of these solvents constitutes an individual embodiment of the invention. The organic solvent is preferably selected from ethanol, glycerol or acetone.

After preparation of the solution comprising a GLP-1 analogue, it is normally placed at ambient temperature, and the crystals will start to form after a while. After formation the crystals are isolated from the mother liquor. The temperature of the solution is easily decided by the skilled practitioner using his common general knowledge, and he may decide to place the solution at a constant temperature, or optionally place the solution at one temperatur and then by step or linear gradient move the temperatur to a lower temperature.

In a further embodiment of the invention the solution is placed at a temperature from about −10° C. to +40° C. In further embodiments of the invention the solution is placed at a temperature from −5° C. to 40° C., −2° C. to 40° C., −1° C. to 40° C., 4° C. to 37° C., or 20 to 25° C. Each of these ranges constitutes an individual embodiment of the invention.

Formation of the crystals may start after 10–60 minutes although it may take a shorter or longer period of time. After formation of the crystals they may be isolated from the mother liquor by filtration, decantation, centrifugation or other means known to the skilled practitioner.

The present invention also relates to crystals, preferably needle shaped crystals, of a GLP-1 analogue obtainable by the process comprising:
a) preparing an aqueous solution comprising a GLP-1 analogue, a salt, and an organic solvent, and
b) isolation of the crystals after formation.

The present invention also relates to needle shaped crystals of a GLP-1 analogue having a length of at least 0.5 $\mu$m. In another embodiment of the invention the crystals are needle shaped crystals of a GLP-1 analogue having a length of at least 2 $\mu$m. In a further embodiment of the invention the crystals are needle shaped crystals of a GLP-1 analogue having a length of 0.5 $\mu$m to 50 $\mu$m, such as 2 $\mu$m to 50 $\mu$m, e.g. 2 $\mu$m to 30 $\mu$m. In a further embodiment of the invention the crystals are needle shaped crystals of a GLP-1 analogue having a length of at least 8 $\mu$m. In a further embodiment of the invention the crystals are needle shaped crystals of a GLP-1 analogue having a length of 8 $\mu$m to 50 $\mu$m.

In a further aspect the present invention relates to a pharmaceutical composition comprising crystals, preferably needle shaped crystals, of a GLP-1 analogue together with a pharmaceutically acceptable carrier or excipient.

The GLP-1 analogues can be produced by a method which comprises culturing or fermenting a host cell containing a DNA sequence encoding the GLP-1 analogue and capable of expressing said analogue in a suitable nutrient medium under conditions permitting the expression of the peptide, after which the resulting GLP-1 analogue is recovered from the culture or fermentation broth. Hereinafter, culturing will be used to cover both culturing and fermenting and the like.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The GLP-1 analogue produced by the cells may then be recovered from the culture medium by conventional procedures including, optionally lysis of cells, separating the host cells from the medium by centrifugation or filtration, precipitating the proteinaceous components of the supernatant or filtrate by means of a salt, e.g. ammonium sulphate, purification by conventional purification techniques, such as chromatographic techniques, if necessary, purification by ion exchange chromatography according to the present invention, and subsequently, subjecting to analytical tests, e.g. PAGE, IEF, if necessary, subjecting to further purification, if necessary, and isolation of the pure GLP-1 analogue.

The DNA sequence encoding the GLP-1 analogue may suitably be of genomic or cDNA origin, for instance obtained by preparing a genomic or cDNA library and screening for DNA sequences coding for all or part of the GLP-1 analogue by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the GLP-1 analogue may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. The DNA sequence may also be prepared by polymerase chain reaction using specific primers, for instance as described in U.S. Pat. No. 4,683,202 or Saiki et al., *Science* 239 (1988), 487–491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the GLP-1 analogue is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the GLP-1 analogue in a variety of host cells are well known in the art, cf. for instance Sambrook et al., supra.

The DNA sequence encoding the GLP-1 analogue may also, if necessary, be operably connected to a suitable terminator, polyadenylation signals, transcriptional enhancer sequences, and translational enhancer sequences. The recombinant vector may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct a GLP-1 analogue into the secretory pathway of the host cells, a secretory signal sequence (also known as a leader sequence, prepro sequence or pre sequence) may be provided in the recombinant vector. The secretory signal sequence is joined to the DNA sequence encoding the GLP-1 analogue in the correct reading frame. Secretory signal sequences are commonly positioned 5' to the DNA sequence encoding the GLP-1 analogue. The secretory signal sequence may be that normally associated with the GLP-1 analogue or may be from a gene encoding another secreted protein.

The procedures used to ligate the DNA sequences coding for the GLP-1 analogue, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the GLP-1 analogue and includes bacteria, vira, e.g. baculo virus, yeast, fungi, insect cells and higher eukaryotic cells. Examples of suitable host cells well known and used in the art are, without limitation, *E. coli*, *Saccharomyces cerevisiae*, or mammalian BHK or CHO cell lines.

Some of the GLP-1 analogue, can be produced according to conventional organic peptide synthetic chemistry. The resulting synthetic mixture may then be chemically modified, e.g. by alkylation, acylation, ester formation or amide formation or the like, and purified, or purified as it is and then modified chemically.

Usually, the fermentation broth comprising the GLP-1 analogue will also contain amino acids, small peptides, large peptides, unrelated proteins, reactants, cell debris, host cell proteins, endotoxins, and/or vira depending on whether recombinant DNA techniques and/or chemical modification techniques have been used or whether organic peptide synthetic chemistry techniques have been used.

Thus, any method, such as an industrial method, for producing a GLP-1 analogue, which includes a crystallization step according to the present invention is also an aspect of the present application.

Accordingly, the present invention relates in a further aspect to a method for producing a GLP-1 analogue or a GLP-1 analogue whereto is attached a lipophilic substituent comprising:
  a) expressing the GLP-1 analogue in a host cell, such as yeast,
  b) precipitating the analogue at its pI,
  c) preparing an aqueous solution comprising the GLP-1 analogue, a salt, and an organic solvent, and
  d) isolation of the crystals after formation, and
  e) further purification, optionally followed by repetition of steps b to e, to isolation of crystals of the GLP-1 analogue, and
  f) optionally acylation of the GLP-1 analogue, optionally followed by purification.

In a further aspect the present invention relates to a process for producing crystals of a GLP-1 analogue comprising:
  a) preparing an aqueous solution comprising a GLP-1 analogue, and a salt, and
  b) isolation of the crystals after formation.

Another invention relates to a process for producing crystals of a GLP-1 analogue comprising:
  a) preparing an aqueous solution comprising a GLP-1 analogue, and a salt, and
  b) isolation of the crystals after formation. Anyone of the above embodiments is also intended to represent embodiments of this invention where possible.

The term "an organic solvent", as used herein, is intended to include any organic solvent which do not denature the GLP-1 analogue. The organic solvent includes but is not limited to $C_{1-6}$-alkanol, $C_{1-6}$-alkenol or $C_{1-6}$-alkynol, urea, guanidine, or $C_{1-6}$-alkanoic acid, such as acetic acid, ketone, such as acetone, dimethylsulphoxide (DMSO), polymeric solvents, $C_{2-6}$-glycol, $C_{3-7}$-polyalcohol including sugars, or mixtures thereof.

The term "$C_{1-6}$-alkanol", "$C_{1-6}$-alkenol" or "$C_{1-6}$-alkynol", as used herein, alone or in combination is intended to include those $C_{1-6}$-alkane, $C_{1-6}$-alkene or $C_{1-6}$-alkyne groups of the designated length in either a linear or branched or cyclic configuration whereto is linked a hydroxyl (—OH) (cf. Morrison & Boyd, Organic Chemistry, $4^{th}$ ed). Examples of linear alcohols are methanol, ethanol, n-propanol, allyl alcohol, n-butanol, n-pentanol and n-hexanol. Examples of branched alcohols are 2-propanol and tert-butyl alcohol. Examples of cyclic alcohols are cyclo propyl alcohol and 2-cyclohexen-1-ol.

The term "$C_{1-6}$-alkanoic acid", as used herein, is intended to include a group of the formula R'COOH wherein R' is H or $C_{1-5}$alkyl, such as acetic, propionic, butyric, α-methylbutyric, or valeric acid (cf. Morrison & Boyd, Organic Chemistry, $4^{th}$ ed).

The term "$C_{1-12}$-alkyl", as used herein, is intended to include a branched or straight alkyl group having from one to 12 carbon atoms. Typical $C_{1-12}$-alkyl groups are $C_{1-5}$-alkyl groups which include, but are not limited to, methyl, ethyl, n-propyl, iso-propyl, butyl, iso-butyl, sec-butyl, tert-butyl, pentyl, iso-pentyl, and the like (cf. Morrison & Boyd, Organic Chemistry, $4^{th}$ ed).

The term "$C_{2-6}$-glycol", as used herein, is intended to include a $C_{2-6}$-alkane containing two hydroxyl groups on different carbon atoms which may be adjacent or not. A typical $C_{2-6}$-glycol include, but is not limited to 1,2-ethanediol, 1,2-propanediol, or 2-methyl-2,4-pentanediol (cf. Morrison & Boyd, Organic Chemistry, $4^{th}$ ed).

The term "$C_{2-6}$-alkane", as used herein, is intended to include a branched or straight alkane group having from two to six carbon atoms. Typical $C_{2-6}$-alkane groups include, but are not limited to ethane, propane, iso-propane, butane, iso-butane, pentane, hexane and the like (cf. Morrison & Boyd, Organic Chemistry, $4^{th}$ ed).

The term "$C_{3-7}$-polyalcohol including sugars", as used herein, is intended to include a group of the formula $HOCH_2(CHOH)_nCH_2OH$ wherein n is an integer from 1–5, and monosaccharides such as glycerol, mannose, glucose (cf. Morrison & Boyd, Organic Chemistry, $4^{th}$ ed).

The term "a GLP-1 analogue", as used herein, is intended to designate GLP-1 (7–37), GLP-1 (7–36) amide as well as analogues, fragments, homologues, and derivatives thereof, which are capable of being produced by conventional recombinant DNA techniques as well as conventional synthetic methods. Such GLP-1 analogues include but are not limited to native glucagon-like peptide-1, for instance such peptide fragments which comprises GLP-1 (7–37) and functional derivatives thereof as disclosed in WO 87/06941; such peptide fragments which comprise GLP-1 (7–36) and functional derivatives thereof as disclosed in WO 90/11296; such analogues of the active GLP-1 peptides 7–34, 7–35, 7–36, and 7–37 as disclosed in WO 91/11457; such N-terminal truncated fragments of GLP-1 as disclosed in EP 0699686-A2; such GLP-1 analogues and derivatives that include an N-terminal imidazole group as disclosed in EP 0708179-A2; and such exendins as disclosed in WO 9746584 and U.S. Pat. No. 5,424,286.

The term "exendins", as used herein, is intended to designate exendin as well as analogs, derivatives, and fragments thereof, e.g. exendin-3 and 4. Examples of exendin as well as analogs, derivatives, and fragments thereof to be included within the present invention are those disclosed in WO 9746584 and U.S. Pat. No. 5,424,286. U.S. Pat. No. 5,424,286 describes a method for stimulating insulin release with exendin polypeptide(s). The exendin polypeptides disclosed include HGEGTFTSDLSKQMEEEAVRLFIE-WLKNGGX; wherein X=P or Y, and HX1X2GTFITSDL-SKQMEEEAVRLFIEWLKNGGPSSGAPPPS; wherein X1X2=SD (exendin-3) or GE (exendin-4)). The exendin-3 and -4 and fragments are useful in treatment of diabetes mellitus (types 1 or 11) and prevention of hyperglycaemia. They normalise hyperglycaemia through glucose-dependent, insulin-independent and insulin-dependent mechanisms. Exendin-4 is specific for exendin receptors, i.e. it does not interact with vasoactive intestinal peptide receptors. WO 9746584 describes truncated versions of exendin peptide(s) for treating diabetes. The disclosed peptides increase secretion and biosynthesis of insulin, but reduce those of glucagon. The truncated peptides can be made more economically than full length versions.

The term "crystals" as used herein, is intended to designate crystals of any shape, such as single needle shaped crystals (which is the same as needle-like crystals), single irregular shaped crystals, single oblong crystals as well as clusters of two or more crystals and mixtures thereof (cf. "Preparation and analysis of protein crystals" by A. McPherson).

The term "non-synthetic GLP-1 analogues" as used herein, is intended to designate a GLP-1 analogue which comprises only naturally occurring amino acid residues and is capable of being produced by recombinant DNA techniques or expressed by organisms, e.g. microorganisms.

The term "ketone" as used herein, is intended to designate a compound of the formula $R^1$—CO—$R^2$ wherein $R^1$ and $R^2$ are independently of each other selected from $C_{1-12}$-alkyl, preferably $C_{1-5}$-alkyl (cf. Morrison & Boyd, Organic Chemistry, $4^{th}$ ed).

The term "polymeric solvents" as used herein, is intended to comprise poly(acrylic acid), carboxymethylcellulose, poly(ethylene glycol), poly(propylene glycol), poly(vinyl alcohol), poly(vinylpyrrolidone) and the like (cf. "Preparation and analysis of protein crystals" by A. McPherson).

The term "analogues" as used herein, is intended to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivatives" as used herein, is intended to designate a peptide in which one or more of the amino acid residues of the parent peptide have been chemically modified, e.g. by alkylation, acylation, ester formation or amide formation or the like.

The term "a salt" as used herein, is intended to include any organic or inorganic salt, including but not limited to NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof (cf. Remington's Pharmaceutical Sciences, Gennaro, ed., Mack Publishing Co., Easton, Pa., 1990, or Remington: The Science and Practice of Pharmacy, 19th Edition (1995), or handbooks from Amersham-Pharmacia Biotech).

The term "a buffer" as used herein, is intended to include any buffer including but not limited to: citrate buffers, phosphate buffers, tris buffers, bis-Tris buffer, borate buffers, lactate buffers, glycyl glycin buffers, arginine buffers, carbonate buffers, acetate buffers, glutamate buffers, ammonium buffers, glycin buffers, alkylamine buffers, aminoethyl alcohol buffers, ethylenediamine buffers, tri-ethanol amine, imidazole buffers, pyridine buffers and barbiturate buffers and mixtures thereof (cf. Remington's Pharmaceutical Sciences, Gennaro, ed., Mack Publishing Co., Easton, Pa., 1990, or Remington: The Science and Practice of Pharmacy, 19th Edition (1995), or handbooks from Amersham-Pharmacia Biotech).

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXPERIMENTAL PART

Crystallisation of $Arg^{34}GLP1_{(7-37)}$ in the Manufacturing Process for Preparing a Mono Acylated GLP-1 Analogue $Arg^{34}GLP1_{(7-37)}$ was expressed in yeast, that is Saccharomyces cerevisiae (Sacch. cerevisiae), by conventional recombinant DNA technology. The fermentation broth was purified by a conventional reverse phase capture step followed by a first precipitation step (precipitate (A)) at the iso-electric point (pI) of $Arg^{34}GLP1_{(7-37)}$. $Arg^{34}GLP1_{(7-37)}$ was then re-dissolved and further purified by conventional High Performance Cation Exchange Chromatography (HP-CIEC) and Reverse Phase High Performance Liquid Chromatography (RP-HPLC) followed by a second precipitation step (precipitate (B)) at the pI of $Arg^{34}GLP1_{(7-37)}$.

Then $Arg^{34}GLP1_{(7-37)}$ was acylated, e.g. as disclosed in WO 98/08871, and the re-suiting solution containing mono-acylated $Arg^{34}GLP1_{(7-37)}$ was further purified by conventional RP-HPLC and finally precipitated at pI of mono-acylated $Arg^{34}GLP1_{(7-37)}$.

The implementation of a crystallisation step in the manufacturing process for the preparation of mono-acylated $Arg^{34}GLP1_{(7-37)}$ results in removal of coloured compounds from the fermentation broth, reduction of Saccharomyces cerevisiae proteins (host cell proteins) (SCP) as well as removal of water, and low loss of $Arg^{34}GLP1_{(7-37)}$ from the mother liquor.

Crystallisation of $Arg^{34}GLP1_{(7-37)}$ from precipitate (A) and precipitate (B) has been performed. An overview of the experiments is given in the following section along with a description of the crystallisation procedure.

General Procedure:

The precipitate (A) from the first precipitation step (or the precipitate (B) from the second precipitation step) was suspended in water and pH was adjusted to pH 8.5–9.5 with NaOH by which the precipitate dissolved. The $Arg^{34}GLP1_{(7-37)}$ concentration (referred to as GLP1 conc. in the tables) of the stock solution was measured by analytical RP-HPLC (Analytical procedure 427-AF006.D02: Purity and Concentration of GLP-1 (Inger Bastholm, 1999)). Then salt, organic solvent and buffer compound was added to the desired concentration and the solution was adjusted to the specified pH with HCl, then gently swirled and placed at the specified temperature (scale: 3–5 ml). Formation of crystals started to occur after 10–60 minutes and after 16–18 hr the crystal morphology was studied in microscope (Microscope BX50 from Olympus). For quantification a portion of the mother liquor was removed and centrifuged. The $Arg^{34}GLP1_{(7-37)}$ content was measured by analytical RP-HPLC. The loss by crystallisation was calculated by division of the supernatant content by the content in the starting material.

N.A.=Not Assessed

| Example precipitate A | GLP1 conc. | Salt | Solvent | Buffer | pH | Temp. | Crystal morphology/size | Loss [%] |
|---|---|---|---|---|---|---|---|---|
| 1 | 3.4 mg/ml | 75 Mm NaCl | None | 6 mM bis-Tris | 6.5 | 20–25° C. | Amorphous precipitate. | 45.6 |
| 2 | " | 75 Mm NaCl | 5% ethanol | 6 mM bis-Tris | 6.5 | 20–25° C. | Irregular shaped. | 13.5 |
| 3 | " | 75 mM NaCl | 10% ethanol | 6 mM bis-Tris | 6.5 | 20–25° C. | Irregular shaped. | 12.4 |
| 4 | " | 75 mM NaCl | 15% ethanol | 6 mM bis-Tris | 6.5 | 20–25° C. | Amorphous precipitate. | 13.0 |
| 5 | " | 150 mM NaCl | None | 6 mM bis-Tris | 6.5 | 20–25° C. | Irregular shaped. | 13.4 |
| 6 | " | 150 mM NaCl | 5% ethanol | 6 mM bis-Tris | 6.5 | 20–25° C. | Irregular shaped, few needle shaped (ca. 5 μm). | 11.2 |
| 7 | " | 150 mM NaCl | 10% ethanol | 6 mM bis-Tris | 6.5 | 20–25° C. | Needle shaped (5–15 μm). | 9.1 |
| 8 | " | 150 mM NaCl | 15% ethanol | 6 mM bis-Tris | 6.5 | 20–25° C. | Amorphous precipitation. | 11.3 |
| 9 | 3.4 mg/ml | 150 mM NaCl | 10% ethanol | 6 mM bis-Tris | 6.6 | 20–25° C. | Needle shaped. | 5.7 |
| 10 | " | 200 mM NaCl | 10% ethanol | 6 mM bis-Tris | 6.6 | 20–25° C. | Needle shaped. | 5.9 |
| 11 | " | 250 mM NaCl | 10% ethanol | 6 mM bis-Tris | 6.6 | 20–25° C. | Needle shaped, clusters. | 5.7 |
| 12 | " | 300 mM NaCl | 10% ethanol | 6 mM bis-Tris | 6.6 | 20–25° C. | Needle shaped, clusters. | 5.1 |
| 13 | 5.6 mg/ml | 150 mM NaCl | 2.5% acetone | 5 mM bis-Tris | 6.5 | 20–25° C. | Small, irregular shaped. | 8.4 |
| 14 | " | 150 mM NaCl | 5% acetone | 5 mM bis-Tris | 6.5 | 20–25° C. | Small, oblong crystals (ca. 5 μm). | 8.2 |
| 15 | " | 150 mM NaCl | 10% acetone | 5 mM bis-Tris | 6.5 | 20–25° C. | Irregular shaped, many needle shaped (7–9 μm). | 8.9 |
| 16 | " | 150 mM NaCl | 2.5% glycerol | 5 mM bis-Tris | 6.5 | 20–25° C. | Small, irregular shaped (1–2 μm). | 8.6 |
| 17 | " | 150 mM NaCl | 5% glycerol | 5 mM bis-Tris | 6.5 | 20–25° C. | Small, irregular shaped (2–3 μm). | 9.5 |
| 18 | " | 150 mM NaCl | 10% glycerol | 5 mM bis-Tris | 6.5 | 20–25° C. | Small, irregular shaped (1–2 μm). | 8.0 |
| 19 | 4 mg/ml | 75 mM NaCl | 5% ethanol | 5 mM bis-Tris | 6.5 | 20–25° C. | Needle shaped. | 4.0 |
| 20 | " | 75 mM NaCl | 5% ethanol | 5 mM bis-Tris | 6.5 | 4° C. | Needle shaped. | 6.5 |
| 21 | " | 75 mM NaCl | 10% ethanol | 5 mM bis-Tris | 6.5 | 20–25° C. | Needle shaped. | 4.3 |
| 22 | " | 75 mM NaCl | 10% ethanol | 5 mM bis-Tris | 6.5 | 4° C. | Needle shaped. | 4.5 |
| 23 | " | 75 mM NaCl | 15% ethanol | 5 mM bis-Tris | 6.5 | 20–25° C. | Needle shaped. | 5.3 |
| 24 | " | 75 mM NaCl | 15% ethanol | 5 mM bis-Tris | 6.5 | 4° C. | Needle shaped. | 6.0 |
| 25 | " | 100 mM NaCl | None | 5 mM bis-Tris | 6.5 | 20–25° C. | Needle shaped. | 3.8 |
| 26 | " | 100 mM NaCl | None | 5 mM bis-Tris | 6.5 | 4° C. | Amorphous. | 7.0 |
| 27 | " | 100 mM NaCl | 5% ethanol | 5 mM bis-Tris | 6.5 | 20–25° C. | Needle shaped. | N.A. |
| 28 | " | 100 mM NaCl | 5% ethanol | 5 mM bis-Tris | 6.5 | 4° C. | Irregular shaped. | 6.0 |
| 29 | " | 100 mM NaCl | 10% ethanol | 5 mM bis-Tris | 6.5 | 20–25° C. | Needle shaped. | 3.3 |
| 30 | " | 100 mM NaCl | 10% ethanol | 5 mM bis-Tris | 6.5 | 4° C. | Needle shaped. | 4.0 |
| 31 | " | 100 mM NaCl | 15% ethanol | 5 mM bis-Tris | 6.5 | 20–25° C. | Needle shaped. | 4.0 |
| 32 | " | 100 mM NaCl | 15% ethanol | 5 mM bis-Tris | 6.5 | 4° C. | Needle shaped, clusters. | 1.3 |
| 33 | " | 200 mM NaCl | None | 5 mM bis-Tris | 6.5 | 20–25° C. | Granular, few needle shaped. | 2.8 |
| 34 | " | 200 mM NaCl | None | 5 mM bis-Tris | 6.5 | 4° C. | Amorphous precipitation. | 2.8 |
| 35 | " | 200 mM NaCl | 10% ethanol | 5 mM bis-Tris | 6.5 | 20–25° C. | Needle shaped. | 2.8 |
| 36 | " | 200 mM NaCl | 10% ethanol | 5 mM bis-Tris | 6.5 | 4° C. | Amorphous, few needle shaped. | 2.0 |
| 37 | " | 300 mM NaCl | None | 5 mM bis-Tris | 6.5 | 20–25° C. | Granular, few needle shaped. | 2.3 |
| 38 | " | 300 mM NaCl | None | 5 mM bis-Tris | 6.5 | 4° C. | Amorphous. | 2.0 |
| 39 | " | 300 mM NaCl | 10% ethanol | 5 mM bis-Tris | 6.5 | 20–25° C. | Needle shaped. | 2.5 |
| 40 | " | 300 mM NaCl | 10% ethanol | 5 mM bis-Tris | 6.5 | 4° C. | Amorphous precipitation, few needle shaped. | 2.0 |
| 41 | 3.3 mg/ml | 100 mM NaCl | 2% ethanol | 5 mM bis-Tris | 6.5 | 20–25° C. | Needle shaped (ca. 7 μm). | N.A. |
| 42 | 3.2 mg/ml | 100 mM NaCl | 5% ethanol | 5 mM bis-Tris | 6.5 | 20–25° C. | Needle shaped (7–11 μm). | 4.9 |
| 43 | 3.2 mg/ml | 100 mM NaCl | 7% ethanol | 5 mM bis-Tris | 6.5 | 20–25° C. | Needle shaped (7–11 μm). | 4.9 |
| 44 | 3.1 mg/ml | 100 mM NaCl | 10% ethanol | 5 mM bis-Tris | 6.5 | 20–25° C. | Needle shaped (7–9 μm). | 5.5 |
| 45 | 2.9 mg/ml | 100 mM NaCl | 15% ethanol | 5 mM bis-Tris | 6.5 | 20–25° C. | Needle shaped (7–9 μm) clusters. | N.A. |
| 46 | 3.2 mg/ml | 200 mM NaCl | 2% ethanol | 5 mM bis-Tris | 6.5 | 20–25° C. | Needle shaped (ca. 7 μm). | N.A. |
| 47 | 3.1 mg/ml | 200 mM NaCl | 5% ethanol | 5 mM bis-Tris | 6.5 | 20–25° C. | Needle shaped (7–11 μm). | 4.7 |
| 48 | 3.0 mg/ml | 200 mM NaCl | 7% ethanol | 5 mM bis-Tris | 6.5 | 20–25° C. | Needle shaped (7–11 μm). | 5.2 |
| 49 | 2.9 mg/ml | 200 mM NaCl | 10% ethanol | 5 mM bis-Tris | 6.5 | 20–25° C. | Needle shaped (7–11 μm). | 6.2 |
| 50 | 2.8 mg/ml | 200 mM NaCl | 15% ethanol | 5 mM bis-Tris | 6.5 | 20–25° C. | Needle shaped (7–9 μm), clusters. | N.A. |
| 51 | 2.6 mg/ml | 75 mM NaCl | 7% ethanol | 5 mM bis-Tris | 6.5 | 20–25° C. | Needle shaped (5–6 μm). | 5.8 |
| 52 | 2.3 mg/ml | 300 mM NaCl | 7% ethanol | 5 mM bis-Tris | 6.5 | 20–25° C. | Needle shaped (9–12 μm). | 5.8 |
| 53 | 3.4 mg/ml | 100 mM KCl | 7% ethanol | 5 mM bis-Tris | 6.5 | 20–25° C. | Needle shaped (4–9 μm). | 4.8 |
| 54 | 3.2 mg/ml | 200 mM KCl | 7% ethanol | 5 mM bis-Tris | 6.5 | 20–25° C. | Needle shaped (4–9 μm), | 4.7 |
| 55 | 3.4 mg/ml | 100 mM $(NH_4)_2SO_4$ | 7% ethanol | 5 mM bis-Tris | 6.5 | 20–25° C. | Needle shaped (7–9 μm). | 5.1 |
| 56 | 3.2 mg/ml | 200 mM $(NH_4)_2SO_4$ | 7% ethanol | 5 mM bis-Tris | 6.5 | 20–25° C. | Needle shaped (4–7 μm). | 5.4 |
| 57 | 0.5 mg/ml | 200 mM NaCl | 7% ethanol | 5 mM bis-Tris | 6.5 | 20–25° C. | Few needle shaped. | 22.5 |
| 58 | 0.6 mg/ml | 200 mM NaCl | 7% ethanol | 5 mM bis-Tris | 6.5 | 20–25° C. | Few needle shaped. | 18.8 |
| 59 | 1.0 mg/ml | 200 mM NaCl | 7% ethanol | 5 mM bis-Tris | 6.5 | 20–25° C. | Few needle shaped. | 11.7 |
| 60 | 1.4 mg/ml | 200 mM NaCl | 7% ethanol | 5 mM bis-Tris | 6.5 | 20–25° C. | Needle shaped. | 8.8 |
| 61 | 2.0 mg/ml | 200 mM NaCl | 7% ethanol | 5 mM bis-Tris | 6.5 | 20–25° C. | Needle shaped. | 4.5 |
| 62 | 3.0 mg/ml | 200 mM NaCl | 7% ethanol | 5 mM bis-Tris | 6.5 | 20–25° C. | Needle shaped. | 4.7 |
| 63 | 5.0 mg/ml | 200 mM NaCl | 7% ethanol | 5 mM bis-Tris | 6.5 | 20–25° C. | Irregular shaped. | 3.0 |

-continued

| Example precipitate A | GLP1 conc. | Salt | Solvent | Buffer | pH | Temp. | Crystal morphology/size | Loss [%] |
|---|---|---|---|---|---|---|---|---|
| 64 | 5.8 mg/ml | 200 mM NaCl | 7% ethanol | 5 mM bis-Tris | 6.5 | 20–25° C. | Amorphous precipitation. | 3.2 |
| 65 | 3.2 mg/ml | 200 mM NaCl | 7% ethanol | 5 mM bis-Tris | 6.0 | 20–25° C. | Needle shaped. | 2.1 |
| 66 | " | 200 mM NaCl | 7% ethanol | 5 mM bis-Tris | 6.2 | 20–25° C. | Needle shaped. | 2.8 |
| 67 | " | 200 mM NaCl | 7% ethanol | 5 mM bis-Tris | 6.6 | 20–25° C. | Needle shaped. | 4.0 |
| 68 | " | 200 mM NaCl | 7% ethanol | 5 mM bis-Tris | 7.0 | 20–25° C. | Needle shaped. | 5.5 |
| 69 | " | 200 mM NaCl | 7% ethanol | 5 mM bis-Tris | 7.2 | 20–25° C. | Needle shaped. | 6.6 |

N.A. = Not Assessed

I claim:

1. A method for producing needle-shaped crystals of Arg$^{34}$GLP-1(7–37) said method comprising placing an aqueous solution of said Arg$^{34}$GLP-1(7–37) at a temperature of between 20–25 degrees centigrade for a time sufficient to allow production of said crystals, wherein said aqueous solution has a pH of between 6 to 7 and comprises in addition to said Arg$^{34}$GLP-1(7–37), 100–200 mM of an inorganic salt and 1–15% (vol/vol) ethanol.

2. The method of claim 1, wherein said aqueous solution contains 2–10 mg/ml of Arg$^{34}$GLP-1(7–37).

3. The method of claim 2, wherein said aqueous solution comprises between 5–10% ethanol (vol/vol).

4. The method of claim 3, wherein said aqueous solution further comprises a buffer.

5. The method of claim 4, wherein said pH of said aqueous solution is between 6.2 and 6.6.

6. The method of claim 5, wherein said inorganic salt is NaCl.

7. The method of claim 4, wherein said buffer is bis-Tris.

8. The method of claim 7 wherein the concentration of said buffer is between 5–10 mM.

9. The method of claim 8, wherein said inorganic salt is NaCl.

10. The method of claim 9 wherein the pH of said aqueous solution is between 6.2 and 6.6.

11. A method for producing an acylated glucagon-like peptide 1 (GLP-1) analogue, said method comprising:

(a) placing an aqueous solution of said GLP-1 analogue at a temperature of between 20–25 degrees centigrade for a time sufficient to allow production of needle-shaped crystals of said GLP-1 analogue, wherein said GLP-1 analogue in said aqueous solution is Arg$^{34}$GLP-1 (7–37) and said aqueous solution has a pH of between 6 to 7 and comprises in addition to said Arg$^{34}$GLP-1 (7–37), 100–200 mM of an inorganic salt and 1–15% (vol/vol) ethanol; and (b) acylating the Arg$^{34}$GLP-1(7–37) that was crystallized in step a).

12. The method of claim 11, wherein the Arg$^{34}$GLP-1 (7–37) in the aqueous solution of step a) was recombinantly expressed in yeast.

13. The method of claim 11, wherein prior to step a) the GLP-1 analogue Arg$^{34}$GLP-1(7–37) is precipitated at a pH of about 5.4.

14. The method of claim 11, wherein said aqueous solution in step a) contains 2–10 mg/ml of Arg$^{34}$GLP-1(7–37).

15. The method of claim 14, wherein said aqueous solution in step a) comprises between 5–10% ethanol (vol/vol).

16. The method of claim 15, wherein said aqueous solution in step a) further comprises a buffer.

17. The method of claim 16, wherein said pH of said aqueous solution is between 6.2 and 6.6.

18. The method of claim 17, wherein said inorganic salt is NaCl.

19. The method of claim 16, wherein said buffer is bis-Tris.

20. The method of claim 19 wherein the concentration of said buffer is between 5–10 mM.

21. The method of claim 20 wherein said inorganic salt in step a) is NaCl.

22. The method of claim 21 wherein the pH of said aqueous solution in step a) is between 6.2 and 6.6.

23. A method for producing crystals of exendin-4, said method comprising placing an aqueous solution of said exendin-4 at a temperature of between 4–37 degrees centigrade for a time sufficient to allow production of said crystals, wherein said aqueous solution has a pH of pI<pH<pI+2 and comprises in addition to said exendin-4, at least 25 mM of a salt and at least 0.5% (vol/vol) organic solvent.

24. The method of claim 23, wherein said aqueous solution contains from 0.5 to 20 mg/ml of exendin-4.

25. The method of claim 23 wherein said aqueous solution comprises 1–15% (vol/vol) of organic solvent.

26. The method of claim 23, wherein said aqueous solution has a pH of pI<pH<pI+2.

27. The method of claim 23, wherein said aqueous solution further comprises a buffer.

28. The method of claim 23, wherein said aqueous solution is place at a temperature of between 20–25 degrees centigrade for a time sufficient to allow production of said crystals.

29. The method of claim 23, wherein said salt is an inorganic salt.

30. The method of claim 29, wherein said inorganic salt is present in said aqueous solution in a concentration of 100–200 mM.

31. The method of claim 23, wherein said aqueous solution contains from 2–10 mg/ml of exendin-4.

32. The method of claim 31, wherein said aqueous solution is placed at a temperature of between 20–25 degrees centigrade for a time sufficient to allow production of said crystals.

33. The method of claim 32, wherein said salt is an inorganic salt.

34. The method of claim 33, wherein said inorganic salt is present in said aqueous solution in a concentration of 100–200 mM.

35. The method of claim 34 wherein said aqueous solution comprises 1–15% (vol/vol) of organic solvent.

36. The method of claim 35, wherein said aqueous solution has a pH of pI<pH<pI+2.

37. The method of claim 36 wherein said aqueous solution further comprises a buffer.

* * * * *